United States Patent [19]

Pujals, Jr.

[11] Patent Number: 4,708,129

[45] Date of Patent: * Nov. 24, 1987

[54] CERVICAL/OCCIPITAL SUPPORT

[76] Inventor: Charles Pujals, Jr., 119 Fayette St., Bridgeton, N.J. 08302

[ * ] Notice: The portion of the term of this patent subsequent to Jan. 7, 2003 has been disclaimed.

[21] Appl. No.: 816,883

[22] Filed: Jan. 7, 1986

Related U.S. Application Data

[63] Continuation-in-part of Ser. No. 563,160, Dec. 19, 1983, Pat. No. 4,562,833.

[51] Int. Cl.⁴ ............................ A61F 5/01; A61F 5/04
[52] U.S. Cl. .................................. 128/75; 128/76 R; 128/87 B; 128/DIG. 23
[58] Field of Search ...................... 128/76 R, 75, 87 B, 128/DIG. 23

[56] References Cited

U.S. PATENT DOCUMENTS

| | | | |
|---|---|---|---|
| 2,806,471 | 9/1957 | Breese | 128/87 B |
| 3,285,243 | 11/1966 | Yellin | 128/DIG. 23 |
| 3,295,516 | 1/1967 | Grassl | 128/75 |
| 3,320,950 | 5/1967 | McElvenny | 128/75 |
| 3,477,425 | 11/1969 | Grassl | 128/75 |
| 3,756,226 | 9/1973 | Calabrese et al. | 128/DIG. 23 |
| 3,850,164 | 11/1974 | Hare | 128/75 |
| 3,957,040 | 5/1976 | Calabrese | 128/75 |
| 4,205,667 | 6/1980 | Gaylord, Jr. | 128/75 |
| 4,502,471 | 3/1985 | Owens | 128/78 |
| 4,520,801 | 6/1985 | Lerman | 128/75 |
| 4,562,833 | 1/1986 | Pujals, Jr. | 128/75 |

Primary Examiner—Edgar S. Burr
Assistant Examiner—Tonya Lamb
Attorney, Agent, or Firm—Hill, Van Santen, Steadman & Simpson

[57] ABSTRACT

A one-piece contoured neck brace or support is disclosed which provides semi-rigid support for a user's head and neck by conforming to and contacting the occiput between the ears, the posterior and lateral neck area and the suprascapular region. The support may be retained on the user's neck by an adjustable strap or collar, and has forwardly extending portions to reduce any uncomfortable pressure on the user's throat. Ear protectors may be selectively attached to the support as needed, as may a head band. The head band may be used to further secure the support, the ear protectors, or both.

20 Claims, 29 Drawing Figures

U.S. Patent Nov. 24, 1987 Sheet 5 of 6 4,708,129
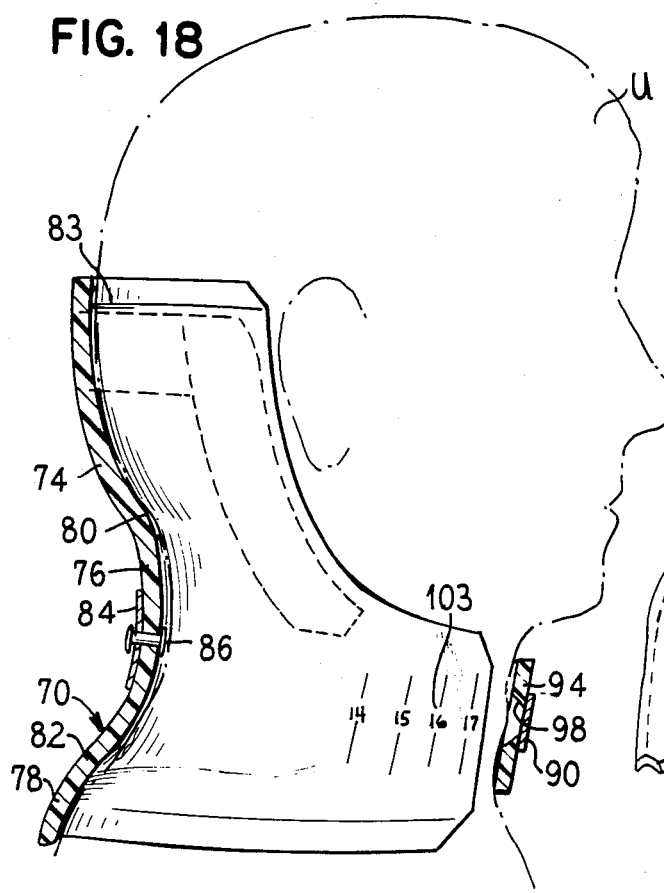
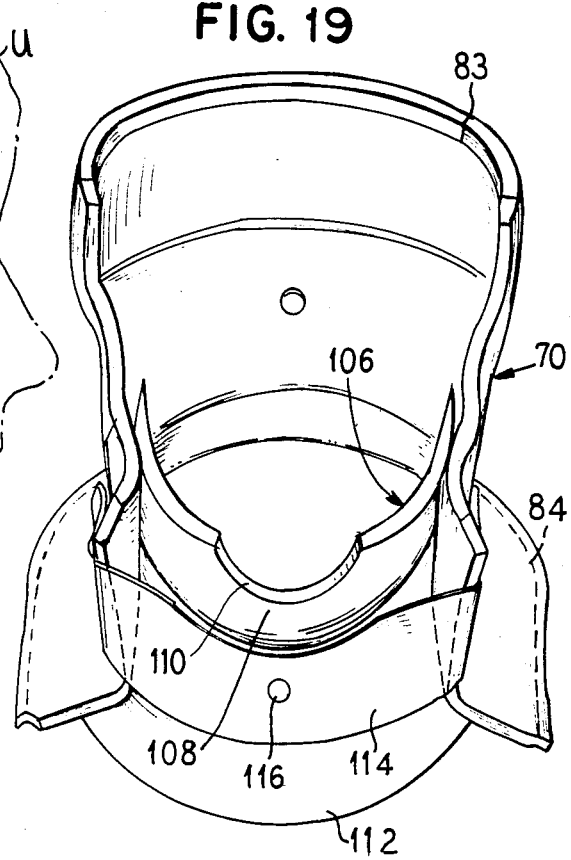
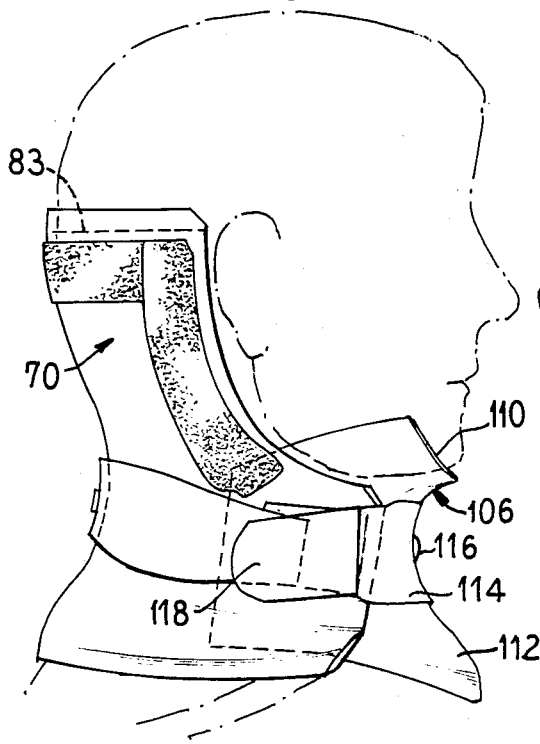
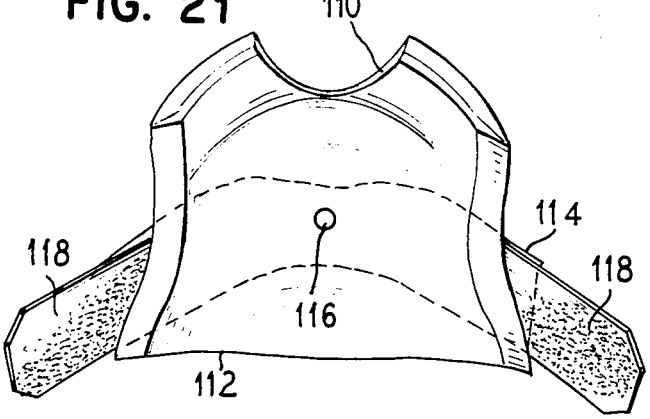
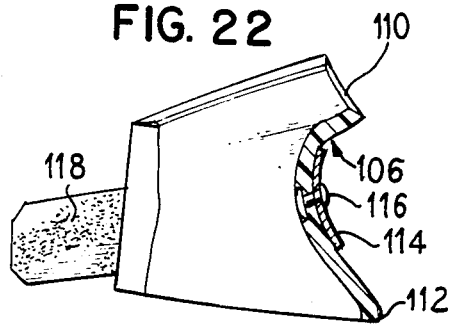

CERVICAL/OCCIPITAL SUPPORT

This application is continuation-in-part of my pending U.S. patent application Ser. No. 563,160 filed Dec. 19, 1983, now U.S. Pat. No. 4,562,833.

BACKGROUND OF THE INVENTION

1. Field of the Invention

The present invention relates to cervical orthopedic devices and more particularly to a semi-rigid neck brace providing posterior and lateral support.

2. Description of the Prior Art

There are presently available several different types of cervical collars or neck braces which are used in the treatment and therapy of cervical trauma. The major problem with fitting foam cervical collars is that there is not adequate support to the neck and skull posteriorly. Various posterior supports have been attempted, but failed to fulfill their purpose of comfortable support. This failure often produces increased muscular tension type headaches, loss of sleep, increased myalgia (muscular aches and pains) and poor posture.

The ideal cervical orthopedic device should support the neck and head as well as allow for postural changes. The presently available collars such as those disclosed in U.S. Pat. Nos. 3,285,243; 3,756,226 and 4,205,667, that do support the head and neck are too limiting and do not allow enough movement to compensate for postural changes. These previous collars are too restrictive causing them to be uncomfortable to wear or tolerate. They fulfill the need for early firm support to limit motion, to prevent further injury of acute surgical trauma or post-operatively. These collars lose some of the support with a decrease in muscle spasm which requires refitting to provide accurate support. Another disadvantage is the spacing of the support away from the skin. The device disclosed in U.S. Pat. No. 3,285,243 does have skin contact limited to the mid-line area of the interscapular area to the basal area of the skull.

These collars are rigid devices to give support, restrict motion and to allow rest to promote healing. Rigid supports have disadvantages in that they increase spasm, decrease blood flow because of the inactivity of muscles, cause swelling of synovial joints in the cervical spine, cause cervical muscle weakness because of restricted motion in injury, are difficult to get proper support for all patients, and do not fit to the skin.

SUMMARY OF THE INVENTION

The present invention provides for a neck brace or support which combines the collar-brace concept. It is a semirigid plastizoate shell contoured to fit the occipital area of the skull and neck posterolaterally to the base of the neck. The addition of controlled recovery foam polyurethane such as Confor R foam or Temper foam assures comfort, adequate fit, and support while allowing postural changes. By allowing these postural changes, there is the advantage of improving the function of joint mechano-receptors and muscles which will decrease spasm and increase blood flow of the involved area.

Adequate support of the head and neck is needed for several reasons. One reason is to unload the skull from the cervical spine without excessive restriction of motion. Secondly, it is important for the body to move enough to maintain muscle function and reduce spasm, reduce swelling, and increase blood flow leading to decreased swelling. Also, the joint mechano-receptor activity via active/passive movement gives greater muscle function for balance around joints, gives support to the skull and improves posture.

The brace—support of the present invention has a tight fit increasing support to the injured muscles and joints, increasing relaxation to injured muscles and joints, and substitutes for muscle function, thereby increasing healing, blood flow and reducing swelling. It decreases nervous system activity, especially muscle spasm, via pressure on the skin mechano-receptors resulting in accomodation leading to decreased muscle tone.

The present neck brace has a U-shaped body construction which follows various contours. It follows the contour of the occiput between the ears usually $\frac{1}{2}-\frac{3}{4}''$ away from the attachment of the ears to the skull, thereby cradling the posterior skull. The U-shaped body also follows the contour of the atlanto-occipital junction attachment of the neck to the skull. Further, the body follows the contour of the posterior lateral neck from atlanto-occipital junction to the base of the neck at the beginning of shoulder level.

The various contours of the brace body are purposefully designed to give the necessary support and rigidity without the addition of an extra reinforcing device to the exterior. In one embodiment of the invention the U-shaped body support is held against the occiput and neck by a foam or plastic collar. As the U-shaped circumference is narrowed to follow the contours of the head and neck, it becomes more rigid, thereby supporting the involved structures in the injured area. In other embodiments of the invention, the brace support body is incorporated into a pillow for use in a reclining position, or multiple brace bodies are nested to provide sufficiently rigid support.

The rigidity attained by the brace body does not totally prevent any motion. It is a gentle rigidity that allows forceful movement when position change will bring relief to the user. One of the purposes and objects of this collar is to allow enough movement by the wearer to maintain joint mechano-receptor activity of the cervical apophyseal joints and surrounding muscles. Another purpose and object of the contour fit is to increase the temperature of the supported area. This is accomplished by the close fit of the collar to the skin, thereby dilating the blood vessels. The increased blood flow hastens healing by decreasing muscle spasm and swelling, thereby allowing adequate healing to take place.

Other embodiments of the present invention include continuously adjustable attachment means such as Velcro ® fastening system straps for holding the brace shell on the user's neck such that the degree of tightness of the shell against the user's neck and head is infinitely adjustable. A special front strap may be utilized which has a recessed area for the larynx and the front wing portions of the shell may have outwardly directed ends to hold the strap away from the front of the neck to relieve pressure on the user's larynx. The shell may also include a plurality of trim lines on the back of the shell corresponding to the spinal area to improve support in patients with postural deformities such as that caused by arthritis or in kyphotic patients.

The shell may also be used with other available chin supports as a front attachment to the shell. Also, ear protectors may be utilized which are attachable to the shell by means of Velcro ® fastening system straps which have a central cut-out portion for receiving the patient's ear and a raised foam ring surrounding the ear which is particularly useful for accident victims who generally have their head restrained during transport from the accident scene to the hospital by means of sand bags placed against the sides of their heads. The ear protectors prevent unnecessary and uncomfortable pressure against the ears caused by the sand bags. The position of the ear protectors is continuously adjustable by means of the Velcro ® fastening system straps.

An abbreviated form of the shell is also provided which does not require the bottom portion of the shell which generally rests upon the patient's shoulders. The abbreviated shell can be held in place on the back of the neck by means of a Velcro ® fastening system attachment to a foam or plastic collar.

BRIEF DESCRIPTION OF THE DRAWINGS

FIG. 18 is a side sectional view of the support shown in FIG. 13.

FIG. 19 is a front elevational view of the support of FIG. 13 including a front chin support member.

FIG. 20 is a side elevational view of the head and neck support and chin support of FIG. 19.

FIG. 21 is a rear elevational view of the chin support shown in FIG. 19.

FIG. 22 is a side sectional view of the chin support shown in FIG. 21.

DESCRIPTION OF THE PREFERRED EMBODIMENTS

Figure 1:
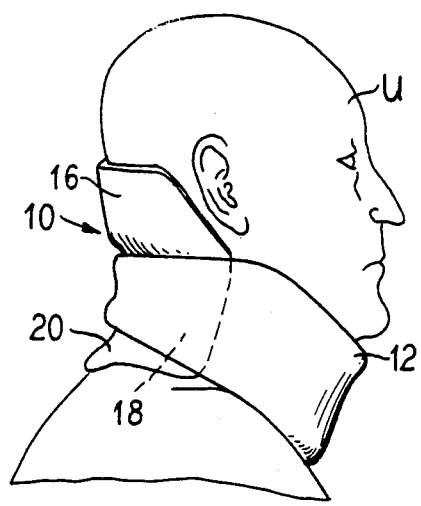
FIG. 1 is a side view of a neck brace embodying the principles of the present invention being worn by a user.
Figure 6:
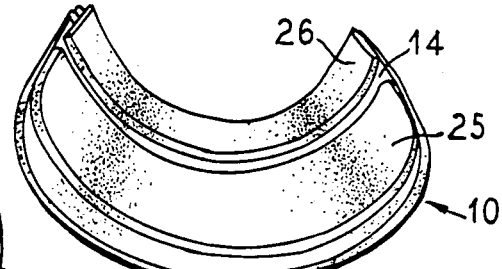
FIG. 6 is a top view of the neck brace of the present invention.

In FIG. 1 there is generally shown a neck brace 10 embodying the principles of the invention which is being worn on the neck of a user U. The brace 10 is held in place by a foam collar 12 which surrounds the user's neck and the brace 10 to hold the brace in close conformity with the posterior region of the user's neck, shoulders and lower skull. As seen in FIG. 6, the brace 10, when viewed from above, is generally U-shaped having an inner-edge or an inner-surface 14 which conforms generally with the posterior neck area of the user. The brace 10 is contoured to provide distinct surface areas for contact with specific anatomical regions of the human body.

Figure 3:
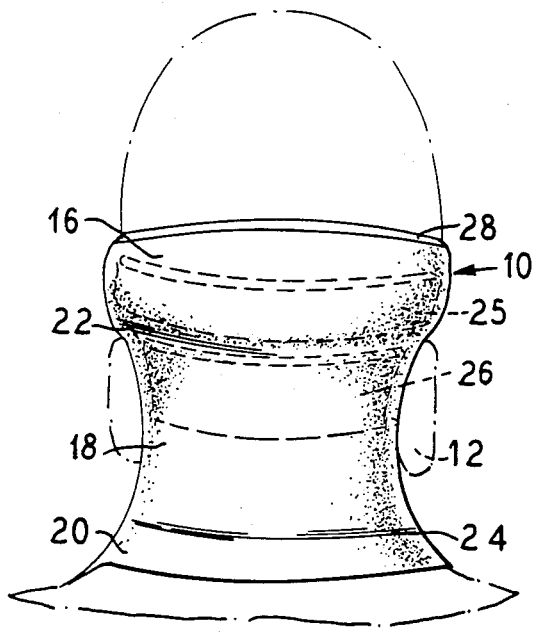
FIG. 3 is a rear plan view of the brace of FIG. 1.

As seen in FIGS. 1 and 3, an upper surface area 16 provides support and cradles the occiput between the ears. This area also prevents hyper-extension at the atlanto-occipital junction. A second central area 18 surrounds and contacts the posterior neck area and a third lower area 20 contacts and rests on the suprascapular region of the user's shoulders. Transition zones 22 and 24 occur between the first and second areas and the second and third areas respectively.

The brace 10 is constructed of a semi-rigid material such as plastizoate and the various contours of the brace not only give the necessary support but also increase the rigidity of the brace 10. The rigidity of the brace is not so great as to totally prevent any motion. The brace does have some resiliency which allows forceful movement when a position change will give relief to the user.

Figure 2:
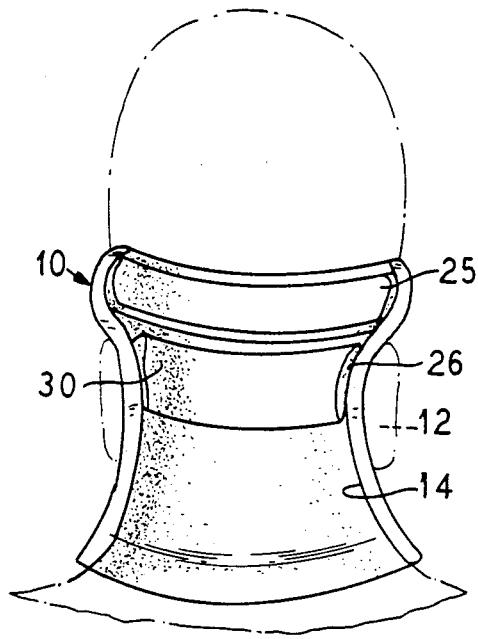
FIG. 2 is a front plan view of the brace of FIG. 1.
Figure 5:
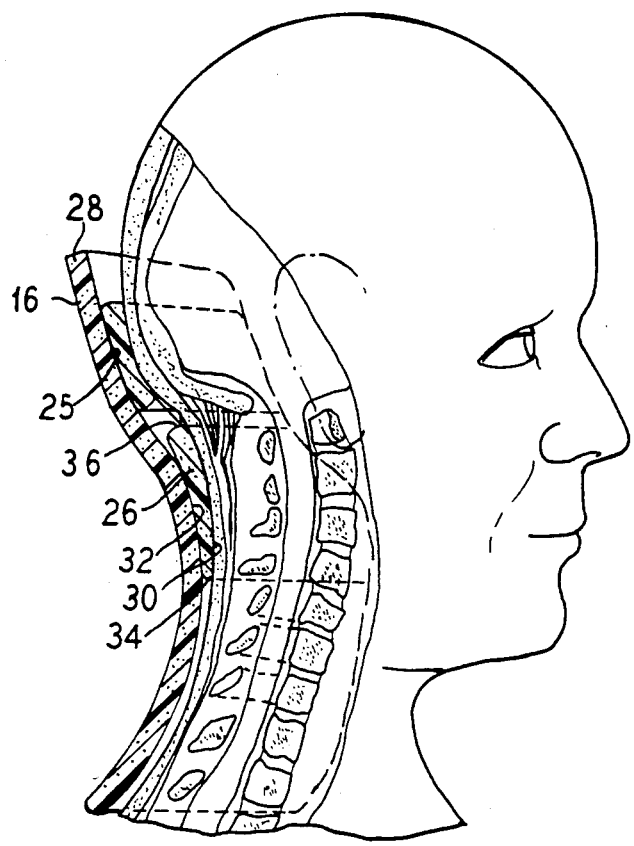
FIG. 5 is a side sectional view of the brace of FIG. 1 and showing a portion of the human anatomy cut away to define the positioning of the brace with respect to the wearer.

In order to increase the comfort of the brace as well as to provide additional support and positive skin contact, one or more foam pads such as those shown at 25 and 26 in FIG. 2 can be supplied on the interior wall 14 of the brace 10. The pads shown in FIGS. 2 and 3 are lateral pads which extend across the width or a portion of the width of the brace 10. The top pad 25 is positioned just below a top end 28 of the brace 10 and is positioned to abut the user's scalp and to overlie the occiput thereby supporting and cradling the occiput. This placement is best seen in FIG. 5 which shows the upper area 16 of the brace with the upper pad 25 positioned laterally just below the top end 28 of the brace 10 and the pad 25 overlying and cradling the occiput.

The second lateral pad 26 is positioned below the top pad 25 and it extends across a portion of the width of the brace 10. The lower pad 26 has a front wall 30 which is at a small angle to a rear wall 32 such that the pad 26 is wedge-shaped with a bottom end 34 being narrower than a top end 36. This wedge-shape more readily conforms to the upper neck and lower skull portion overlying the atlanto-occipital junction in the region of the first through third cervical vertebrae.

The first cervical vertebrae C1 or atlas is a ring-shaped body which is positioned above and receives the odontoid process or dens of the second cervical vertibrae C2 or axis. The neck is comprised of several cervical vertebrae and movement of the neck depends upon the composite movement of all of the vertebrae. Multiple movments of the cervical spine are possible; lateral rotation which is turning the chin to the shoulder occurs mainly between the first and second vertebrae; flexion, which is movement of the chin toward the sternum; extension, which is movement of the occiput backward so that it approximates the cervical spinous process; and lateral bending which is a movement of the ears toward the shoulders while looking straight ahead.

During the treatment and therapy of cervical trauma, it is necessary to immobilize the neck and also to support the head while the injured area heals. In some types of therapy, although the neck is immobilized, some motion is important to allow the body to move enough to maintain muscle function and reduce spasm, reduce swelling and increase blood flow which leads to decreased swelling. The brace 10 of the present invention provides this limited motion while at the same time providing the restriction and support required in the treatment of the trauma.

Figure 4:
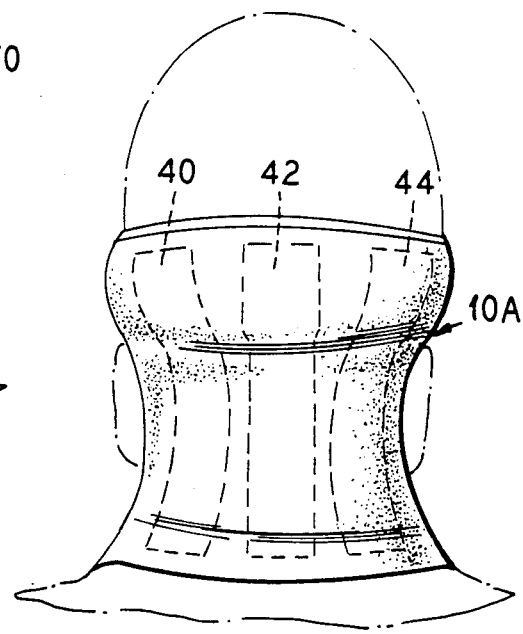
FIG. 4 is a rear plan view of an alternate embodiment of the brace of FIG. 1.

An alternative embodiment of the brace is shown in FIG. 4 at 10A where it is seen that the body or shell of the brace is virtually identical to that shown in FIGS. 1-3, 5. The difference with the brace in FIG. 4 is that the supporting pads run longitudinally as are indicated by their showing in phantom at 40, 42 and 44. Three longitudinal pads are shown which will provide support at specific areas. The middle pad 42 overlies the posterior portion of the cervical vertebrae and occiput and applies pressure against the vertebrae against the spinous processes of the vertebrae. The left and right lateral pads 40 and 44 apply pressure to and support to the lateral muscles and joint capsules of the vertebrae. The thickness of the lateral pads can be adjusted to further the lateral movement within the brace. The polyurethane foam used for the pads is pliant and resilient and conforms to the contours of the adjoining area, therefore although the bony prominences of the posterior spinous processes have the most pressure applied to them, there is also pressure applied in the depressions between the prominences.

The longitudinal pads are spaced apart which allows for movement and swelling in the neck area. The brace body 10 could be provided with a full foam liner covering the entire interior surface 14 instead of multiple foam strips.

Figure 7:
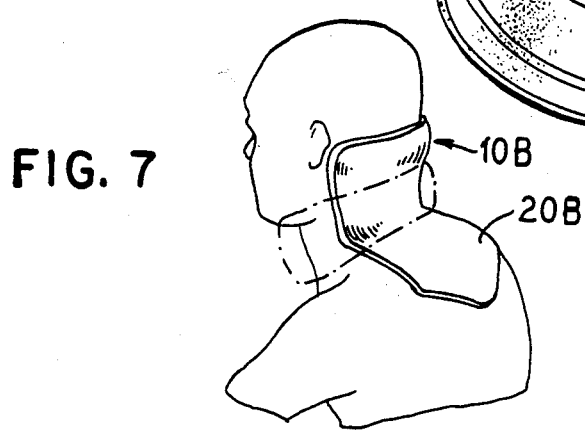
FIG. 7 is a perspective view of a second alternative embodiment of the present invention.

A further alternative embodiment is shown in FIG. 7 which shows the brace 10B having a slightly different configuration of the outer shell. In this embodiment, the lower area 20B extends farther onto the suprascapular region of the shoulders and also extends a portion of the way down the vertebra region. This embodiment with the extended lower area 20B provides additional support against extension. This brace 10B, like those described above, can be utilized with the shell alone, or with the lateral, longitudinal or complete padding as described above or a nested shell for increased support as described below.

The thickness of the pads can be selected and adjusted to put the neck into flexion or extension as required.

Figure 8:
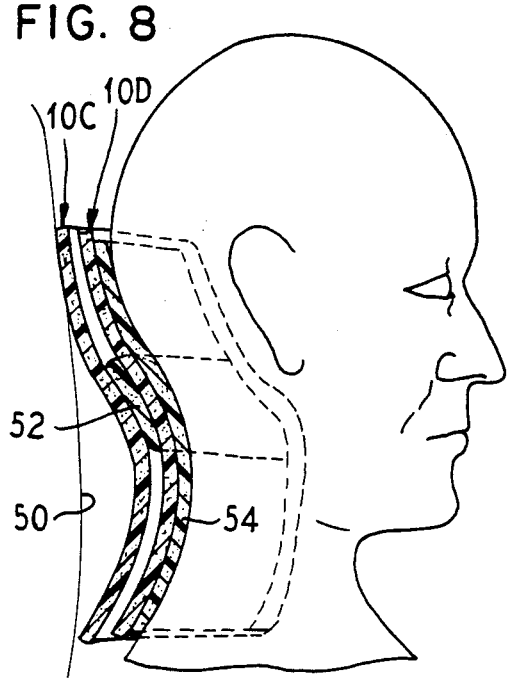
FIG. 8 is a side sectional view of an alternate embodiment of the present invention.

In FIG. 8, there is shown an alternate method of using the neck brace, wherein two brace shells 10C and 10D which are nested, one within the other, to provide additional rigidity to the brace support. The brace can be utilized in this manner when the user is sitting in a substantially upright position such as in a chair with a high back or in an automobile with a head rest and also in a reclining position, for instance in bed, such that the nested braces 10C, 10D are held in place between the user's head and neck and the adjacent surface 50. In the embodiment shown in FIG. 8, a one-piece lateral pad 52 is provided between the two brace shells 10C and 10D. This pad 52 is placed in the sub-occipital area so that there will be a rocking effect between the shells to increase the adjustability and movement of the shells. A larger one-piece pad 54 covering substantially the entire interior surface of the inner shell 10D is provided to engage the user's head and neck area.

Figure 9:
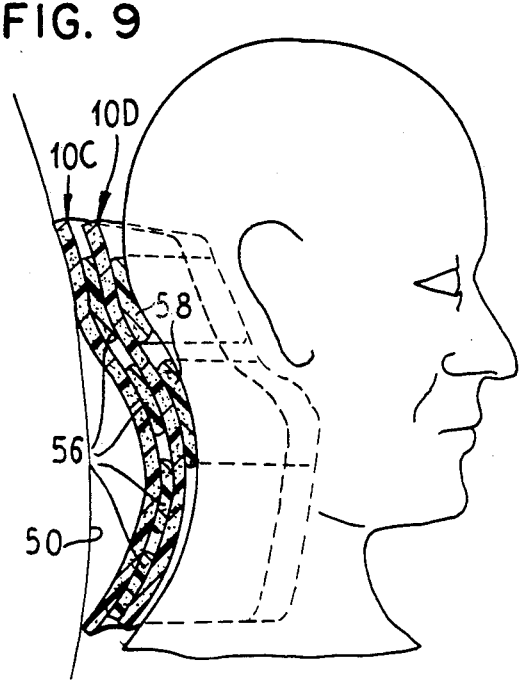
FIG. 9 is a side sectional view of an alternate embodiment of the present invention similar to that shown in FIG. 8.

In FIG. 9, the same nested shells 10C and 10D are provided, but between the two nested shells there are one or more horizontal pad strips 56 and between the inner shell 10D and the user's head and neck there are provided a second plurality of pad strips 58. As described above, these pads may be selectively placed and sized to achieve the desired therapeutic results.

As seen in FIG. 9, the nested shells 10C and 10D may have different lateral dimensions, that is, the inner shell 10D may extend further laterally around the user's neck than the outer shell 10C. In this manner, the outer shell 10C provides the necessary strength and support without detracting from the lateral flexibility provided by the brace.

The use of the brace support shells are shown in FIG. 9 is particularly beneficial when the user is to be seated or reclining in a relatively stationary position for a given period of time. The brace supports provide sufficient support to increase comfort without requiring the confinement and immobility such as when the foam collar is used to secure the brace.

Figure 10:
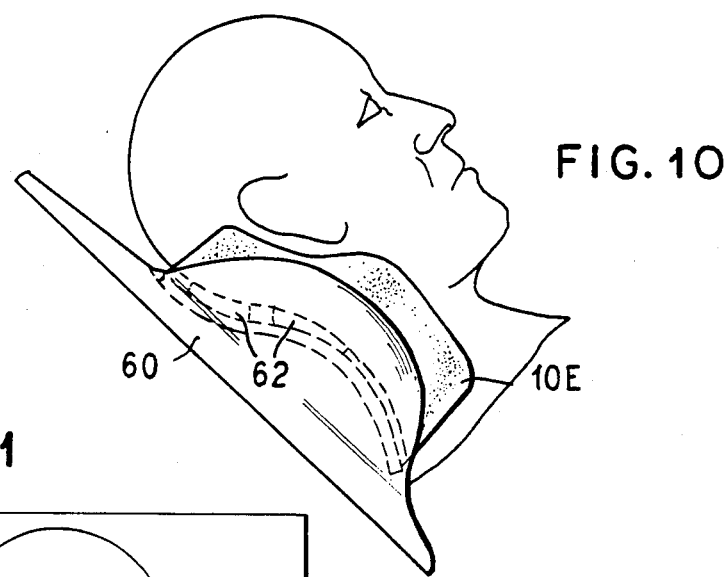
FIG. 10 is a side elevational view of a further alternate embodiment of the present invention.
Figure 11:
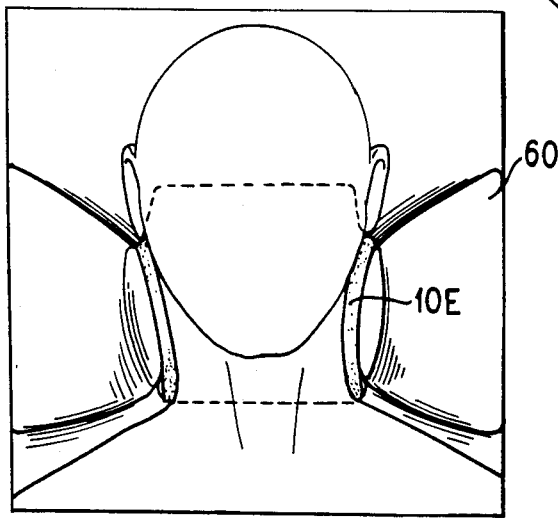
FIG. 11 is a front elevational view of the device shown in FIG. 10.
Figure 12:
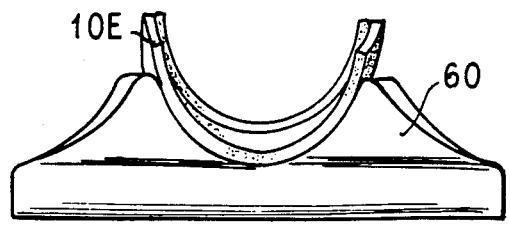
FIG. 12 is an end view of the device shown in FIG. 11.

A further use for the brace shell support is shown in FIGS. 10 through 12 in which the shell 10E is placed in a contoured pillow 60 so that the shell 10E will be held in a fixed orientation relative to the pillow such that the brace will be securely held against the user's head and neck area when user is in a reclining or semi-reclining position. Although FIG. 10 shows two lateral pad strips 62 placed within the shell body, any of the padding arrangements described above could be utilized in this configuration.

This use of the brace shell 10E again provides support for the head and neck area when the user is in a reclining or semi-reclining position for a period of time without the confinement and awkwardness of the foam collar to hold the brace in place.

Figure 13:
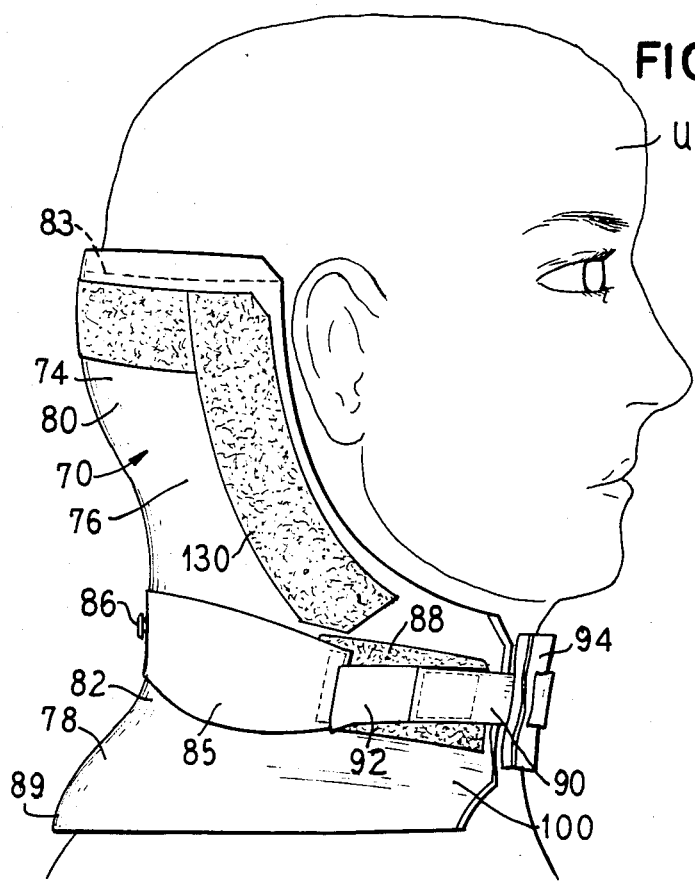
FIG. 13 is a side elevational view of a head and neck support embodying the principles of the present invention held on by an improved retaining means.
Figure 16:
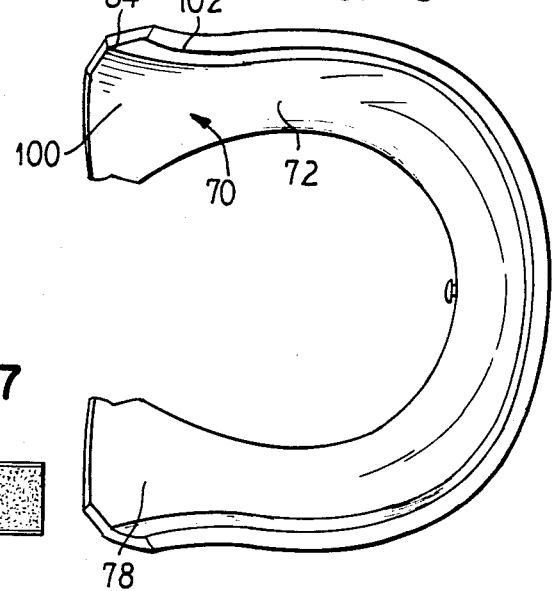
FIG. 16 is a bottom elevational view of the support shown in FIG. 13.

FIG. 13 illustrates an improved cervical/occipital support or shell 70 which, similar to the neck brace 10 described with respect to FIGS. 1-12 is worn on the neck of a user U and is held in close conformity with the posterior region of the user's neck, shoulders and lower skull. As seen in FIG. 16, the support 70, when viewed from below (or above), is generally U-shaped having an inner-edge or an inner-surface 72 which conforms generally with a posterior neck area of the user. The support 70 is contoured to provide distinct surface areas for contact with specific anatomical regions of the human body.

As seen in FIGS. 13 and 18, an upper area 74 provides support and cradles the occiput between the ears. This area also prevents hyper-extension at the atlanto-occipital junction. A second central area 76 surrounds and contacts the posterior lateral neck area. A third lower area 78 contacts and rests on the base of the neck and suprascapular region of the user's shoulders and continues anteriorly to rest on clavicles. Transition zones or contours 80 and 82 occur between the first and second areas and the second and third areas respectively.

The support 70 is constructed of a semi-rigid material such as plastizoate and the various contours 80, 82 of the support not only give the necessary support but also increase the rigidity of the support 10. Additional contours 83, 84 are provided closely adjacent the top and bottom edges of the support 70 to further increase the rigidity. Contour 84 prevents the bottom edge of the support 10 from turning up. The rigidity of the brace is not so great as to totally prevent any motion. The brace does have some resiliency which allows forceful movement when a position change will give relief to the user.

An improved means for retaining the support 70 on the user's neck is illustrated in FIGS. 13-18 which includes an encircling strap 85 secured by an appropriate retaining means 86 such as a rivet to the support which has at its forward ends a pad area 88 comprising the hook portion of a Velcro fastening system. The hook pad area 88 may be fastened to the support 70 such as by stitching. A removable strap 90 which can be made, of an elastic material has a section 92 of loop material of a Velcro fastening system attached at either end of the strap which is engagable with the hook portion 88. In this manner, there is infinitely continuous adjustment of the strap 90 relative to the support 70.

Figure 17:
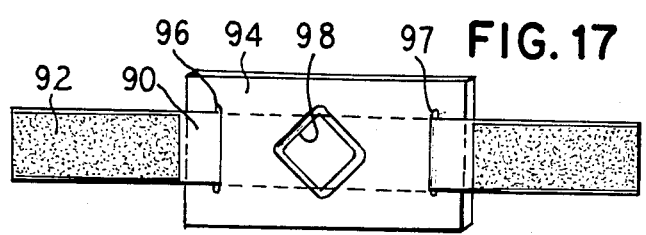
FIG. 17 is a rear elevational view of the retaining strap shown in FIG. 13.

A throat pad 94, shown in greater detail in FIG. 17, is carried on the strap 90 by means of a pair of slits 96, 97 formed in the pad through which the strap 90 passes. The pad is to be positioned at the front of the user's neck to overlie the user's laryngeal prominence and a central portion 98 of the pad is relieved to provide clearance for the laryngeal prominence.

Figure 14:
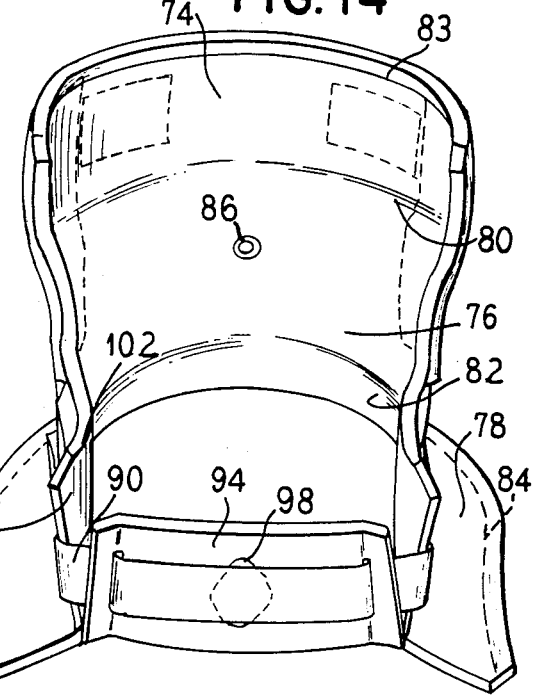
FIG. 14 is a front elevational view of the support shown in FIG. 13.

The support 70 has forwardly extending side wings or extensions 100 which extend forwardly of the user's ears, almost to the front of the user's neck but are short of providing a complete encircling of the user's neck. As seen in FIG. 14, a very front end 102 of the wings 100 is curved outwardly at 102 which further assists in holding the throat pad 94 away from the user's laryngeal prominence. Thus, the support 70 can be held against the user's head and neck quite securely without resulting in excessive pressure or discomfort to the user by engagement with the user's laryngeal prominence.

The extensions 100 can also be provided with markings and trim lines 103 corresponding, for example, to shirt sizes so that the brace may be altered to provide a customized fit for additional comfort to the user.

Figure 15A:
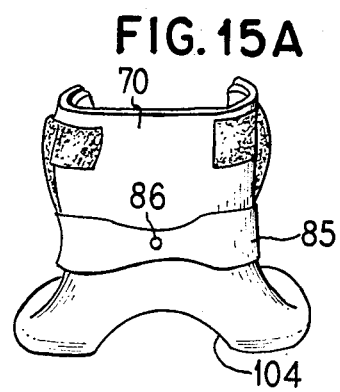
FIG. 15A is a rear perspective view of the support shown in FIG. 13 with a rear trim area removed.
Figure 15:
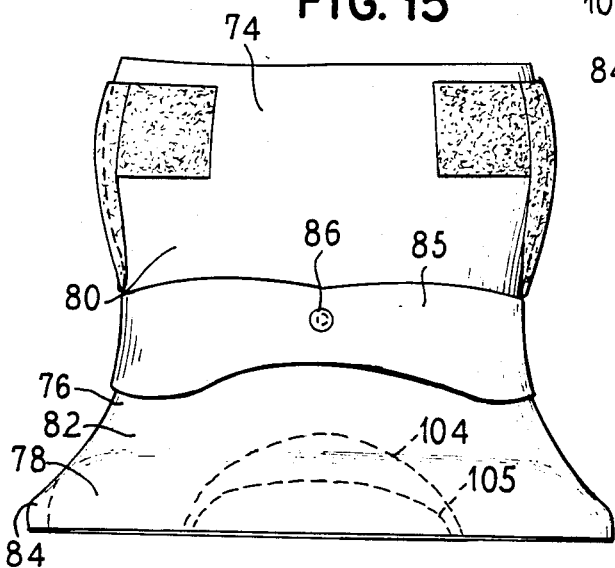
FIG. 15 is a rear elevational view of the support shown in FIG. 13 also showing trim lines.

As seen in FIG. 15, a further improvement includes the provision of trim lines 104, 105 on the rear portion of the support at the lower area 78. These trim lines are included to allow the person fitting the support 70 on the patient to make the support fit more closely in the event that the upper spinal area of the patient is more pronounced especially in patients who have a postural deformity such as elderly arthritic or kyphotic patients. It should also be understood that it is within the scope of the present invention to provide a special model which is made with the trim area already removed from the support 70 as shown in FIG. 15A which provides a recessed portion arranged to overlie the lower cervical and upper thoracic spinal area of the user to provide a clearance for that spinal area.

FIGS. 19-22 illustrate another means for retaining the support 70 on the neck of the user which includes a chin support shell 106 which includes a pocket area 108 for receiving the user's chin, including a cut-out or removed area 110 to provide clearance for the front of the user's chin to prevent jaw discomfort particularly at the temporo-mandibular joint. A bottom end 112 of the chin support shell is arranged to rest on the user's upper chest to provide additional restraint against flexion of the user's neck.

The chin support shell 106 has a strap 114 secured thereto by appropriate fastening means 116 such as a rivet and has a pad section 118 at either end of the strap 114 which is a loop portion of a Velcro fastening system which is secured to the hook portion 88 of the Velcro fastening system attached to the support 70. Thus, the position of the chin support shell 106 is infinitely and continuously adjustable.

Figure 23:
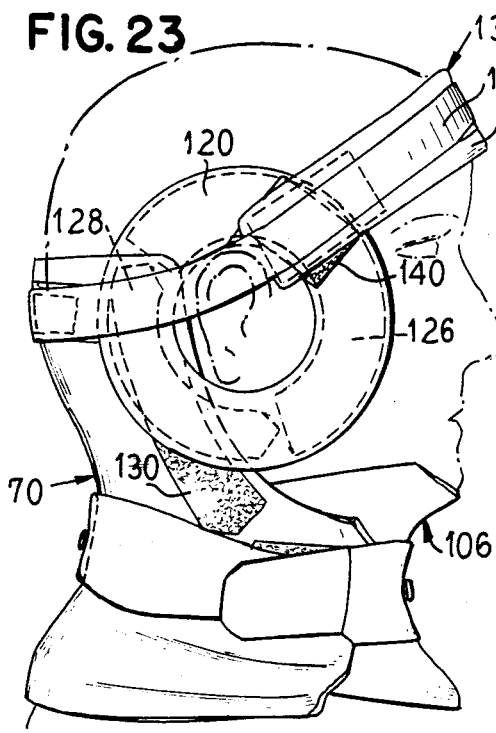
FIG. 23 is a side elevational view of the head and neck support and chin support of FIG. 19 and further including attached ear protectors and head band.
Figure 24:
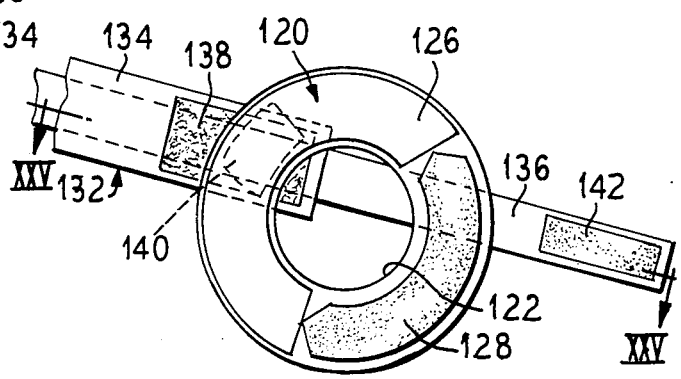
FIG. 24 is a side elevational view of the ear protector shown in FIG. 23.
Figure 25:
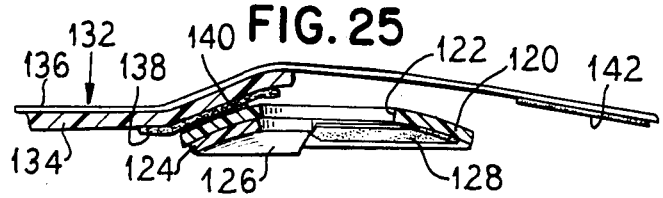
FIG. 25 is a top sectional view of the ear protector taken generally along the lines XXV—XXV of FIG. 24.

FIGS. 23-25 illustrate an additional attachment for the support 70 which includes a pair of ear protectors 120 which are generally ring shaped members having a central opening 122 sized to receive a human ear. A portion of an interior surface 124 of the ear protector 120 may be covered with a cushioning material 126 such as T-foam or Conform R foam, described above, to provide a self adjusting pad for close engagement of the ear protector 120 against the side of the user's head. The thickness of the pad 126 can be selected to provide the necessary protection of the ear as well as the conforming function. If needed, a second layer of foam could be utilized. Another portion of the interior surface 124 of the ear protector 120 has a pad 128 of Velcro fastening system hook material which is engagable with a pad 130 of Velcro fastening system loop material which has been fastened to the exterior surface of the support at the area adjacent the ear. In this manner, the ear protectors 120 can be placed over the patient's ears and attached to the support 70 in an infinitely variable number of positions to provide for accurate placement and positioning of the ear protector to provide maximum comfort.

The use of the ear protectors is especially helpful in the case of accident victims being transported from the scene of an accident to a hospital or other health care facility in that it is customary practice to immobolize the patient by placing the patient's head between sand bags or other relatively immobile restraining devices. Generally, this causes a painful pressure against the patient's ears which the use of the ear protectors will prevent. Thus, the sand bags will engage against the ear protectors to restrain the head from movement, but the ears will be free from compression due to the openings 122 in the protectors. The use of the internal pads 126 will provide a gentle but firm engagement of the protector against the user's head. The ear pads may also be useful where sand bags or other similar restraining devices are utilized such as during the taking of x-ray head is restrained in the hospital bed. It is advantageous that the ear protectors are easily removable so that they can be removed when not required.

A head band 132 may also be used to hold the top end 74 of the support tightly against the occiput and also to ensure that the ear protectors 120 are held in place. The head band 132 includes a central portion 134 which may be made of a foam or absorbent material to engage the user's forehead. An elastic strap 136 is attached to the central portion 134. An interior surface of the central portion 134 has at each end a pad 138 of Velcro fastening system loop material which is adjustably engagable with a pad 140 of Velcro fastening system hook material attached to the exterior of the ear protectors 120. In this fashion, the head band 132 is attached to the ear protectors.

The elastic strap 136 has a pad 142 of Velcro fastening system hook material attached at either end to adjustable engage the pad 130 of Velcro fastening system hook material attached to the exterior surface of the support 70. In this fashion, the head band 132 is attached to the support. The attachment of the head band 132 to the support 70 occurs at the top portions 74 and generally at the lateral posterior region of the support 70 such that the support will be held closely adjacent to the user's occiput. The head band 132 can be used with or without using the ear protectors 120 (FIG. 26).

Figure 26:
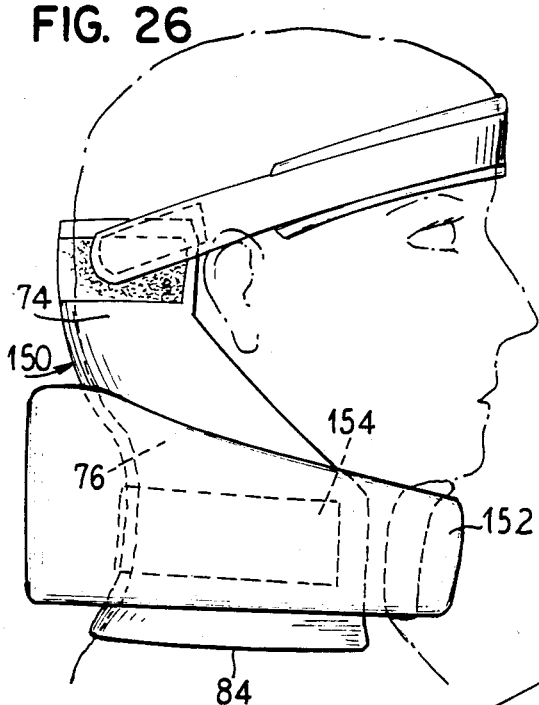
FIG. 26 is a side elevational view of an alternative embodiment of the neck brace held on by an encircling collar.
Figure 27:
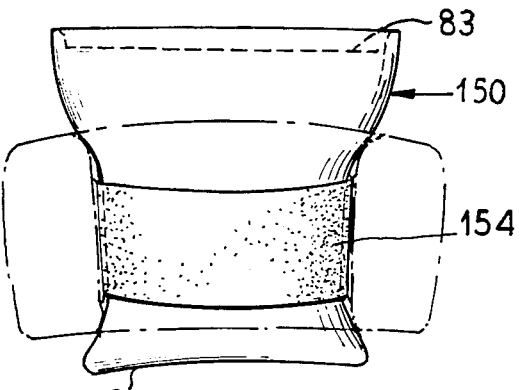
FIG. 27 is a rear elevational view of the brace shown in FIG. 26.
Figure 28:
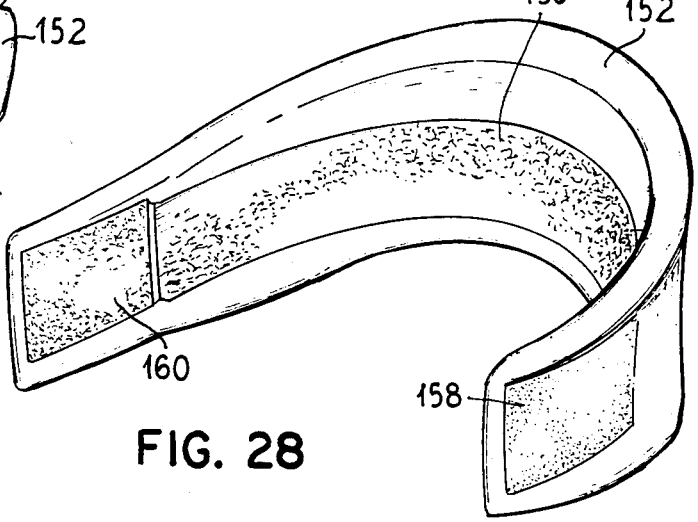
FIG. 28 is a perspective view of the retaining collar used in FIG. 26.

An alternate embodiment of the support is shown in FIGS. 26 and 27 at 150. This embodiment is virtually identical to the support 70 described with respect to FIGS. 13–25, in the upper two thirds of that support, in that the embodiment of FIGS. 26 and 27 includes the upper region 74 and central region 76, but the lower region 78 has been reduced by trimming along contour 84 To hold the modified support 150 on the user's head and neck area, an encircling collar 152 is utilized. The support 150 may have a pad 154 of Velcro fastening system hook material secured thertto on an exterior surface and the collar 152 has a pad 156 of Velcro fastening system loop material on an interior surface to securely, but adjustably hold the collar 152 on the support 150. An additional hook pad 158 and loop pad 160 of Velcro fastening system material may be attached to ends of the collar 152 to provide for an adjustable positioning or tightening of the collar around the user's neck. The encircling collar attaching means illustrated in FIGS. 26–28 can also be used for the previously described embodiments of the head and neck support.

As is apparent from the foregoing specification, the invention is susceptible of being embodied with various alterations and modifications which may differ particularly from those that have been described in the preceeding specification and description. It should be understood that I wish to embody within the scope of the patent warranted hereon all such modifications as reasonably and properly come within the scope of my contribution to the art.

I claim as my invention:

1. A cervical and occipital support for use in supporting a user's head and neck, comprising:
   a semi-rigid preformed U-shaped shell fabricated of a solid, resilient material, contoured to fit the occipital bone area of the skull posterolaterally and the neck posterolaterally to the base of the neck having:
   a first end portion having a first radius of curvature defining said U-shape for laterally supporting and cradling the occipital bone between the ears;
   a central portion having a second radius of curvature smaller than said first radius of curvature for surrounding and contacting the posterior and lateral neck area from the sub occipital area to the base of the neck;
   said central portion including forwardly extending portions which extend along the lateral portions of the user's neck forwardly of the user's ears, but which stop short of completely encircling the user's neck;
   a first transition zone between said first end portion and said central portion spaced from said first end having a decreasing radius of curvature in the direction of said central portion for receiving and longitudinally supporting the occipital bone;
   a second end portion having a third radius of curvature larger than said second radius of curvature for contacting and resting on the suprascapular region and contacting the base of the neck anteriorly and resting on the clavicles;
   a second transition zone between said central portion and said second end portion and having an increasing radius of curvature in the direction of said second end; and
   a retaining means selectively attachable to said support for extending around the exterior portion of the user's neck;
   whereby said user's head and neck are supported by said support without completely immobilizing those areas and said solid material acts to retain the user's body heat.

2. The device of claim 1 including at least one trim line on said second end portion in an area arranged to overlie the lower cervical and upper thoracic spinal area of said user, said trim line indicating a portion of said support which may be trimmed away to provide a clearance for said spinal area.

3. The device of claim 1 including a recessed portion at said second end portion in an area arranged to overlie the lower cervical and upper thoracic spinal area of said user to provide a clearance for said spinal area.

4. The device of claim 1 wherein said retaining means comprises a strap carrying a chin support shell which is selectively attachable to said extending portions of said support.

5. The device of claim 1 including a head band selectively attachable to said first end portion of said support to further retain said first end against the user's occipital bone.

6. The device of claim 1 wherein said retaining means comprises a foam or plastic collar adapted to encircle the user's neck.

7. The device of claim 6 wherein said support and said collar are each provided with an attachment means for selectively attaching said collar to said support.

8. The device of claim 1 wherein said retaining means comprises an elastic strap selectively attachable to said forwardly extending portions of said support.

9. The device of claim 8 including a throat pad carried on said strap engageable with the user's throat and having a recessed portion to overlie the user's larengeal prominence.

10. The device of claim 1 including a pair of ear protectors selectively attachable to said support, each of said ear protectors comprising a concave ring member with a central opening sized to receive a human ear.

11. The device of claim 10 including a head band selectively attachable to said first end portion of said support and to said ear protectors to further retain said first end against the user's occipital bone and the ear protectors around the user's ears.

12. The device of claim 10 wherein said ear protectors include an interior foam pad covering at least a portion of said ring to engage with said user's head adjacent the ear.

13. The device of claim 10 wherein said ear protectors are adjustable positionable on said support to provide adjustability for user comfort.

14. The device of claim 13 wherein said ear protectors are retained on said support by Velcro fastening system.

15. A single piece neck support being constructed and so shaped as to conform substantially to and overlie and be in contact with the occipital bone between the ears at a first end portion having a first radius of curvature defining a lateral U-shape, the posterior and lateral neck area at a central portion having a second radius of curvature smaller than said first radius of curvature, wherein said central portion extends to a termination thereof on the lateral sides of the neck forwardly of the ears, but short of completely encircling the neck, and a portion of the suprascapular region at a second end portion having a third radius of curvature larger than said second radius of curvature, said support being a semi-rigid, resilient shell preformed to the above shape to support and hold the user's head in a desired position, yet flexible enough to allow forceful movement and position change by the user, said support further having a preformed first transition zone between said first end portion and said central portion having a decreasing radius of curvature in the direction of said central portion and a preformed second transition zone between said central portion and said second end portion and having an increasing radius of curvature in the direction of said second end which assist in providing the required support and rigidity to support the user's head.

16. A support according to claim 15, wherein said first end forms an arc of sufficient lateral dimension to engage the occipital bone and to extend to within three-fourths of an inch of the attachment of the user's ears to the skull.

17. A support according to claim 16, wherein a forward edge of said shell is angled rearwardly at said first end to provide clearance for the user's ears.

18. A cervical and occipital support for use in supporting a user's head and neck, comprising:
a semi-rigid preformed U-shaped shell fabricated of a solid, resilient material, contoured to fit the occipital bone area of the skull posterolaterally and the neck posterolaterally to the base of the neck having;
a first end having a first radius of curvature and extending laterally defining an open arc;
a central portion having a second radius of curvature smaller than said first radius of curvature and extending laterally to define an open arc for surrounding and contacting the posterior and lateral neck area from the sub-occipital area to the base of the neck wherein said central portion extends to a termination thereof on the lateral sides of the neck forwardly of the user's ears, but short of completely encircling the user's neck;
a first end portion extending longitudinally from said first end toward said central portion and having a gradually decreasing radius of curvature in the direction of said central portion for laterally supporting and cradling the occipital bone between the ears;
a first transition zone between said first end portion and said central portion and having a rapidly decreasing radius of curvature in the direction of said central portion for receiving and longitudinally supporting the occipital bone;
a second end having a third radius of curvature larger than said second radius of curvature;
a second transition zone between said central portion and said second end and having an increasing radius of curvature in the direction of said second end;
a reinforcing contour formed in said support closely adjacent said second end to prevent said second end from turning up; and
a forward edge along a portion of the perimeter of said shell interconnecting said portions and zones; whereby said transition zones add rigidity to said shell in a longitudinal direction and said solid material acts to retain the user's body heat.

19. A support according to claim 18, wherein said first end forms an arc of sufficient lateral dimension to engage the occipital bone and to extend to within three-fourths of an inch of the attachment of the user's ears to the skull.

20. A support according to claim 19, wherein said forward edge of said shell is angled rearwardly at said first end to provide clearance for the user's ears.

* * * * *